United States Patent
Aldana Moraza et al.

(10) Patent No.: US 9,688,633 B2
(45) Date of Patent: Jun. 27, 2017

(54) SUBSTITUTED PIPERIDINES WITH ANTIPARASITIC ACTIVITY

(71) Applicant: INSTITUT DE RECHERCHE POUR LE DEVELOPPEMENT, Marseille (FR)

(72) Inventors: Ignacio Aldana Moraza, Pamplona (ES); Silvia Victoria Blair Trujillo, Medellin (CO); Eric Deharo, Auterive (FR); Giovanny Garavito, Bogota (CO); Adela Mendoza Lizaldez, Pamplona (ES); Silvia Perez-Silanes, Pamplona (ES)

(73) Assignee: INSTITUT DE RECHERCHE POUR LE DEVELOPPEMENT, Marseille (FR)

( * ) Notice: Subject to any disclaimer, the term of this patent is extended or adjusted under 35 U.S.C. 154(b) by 0 days.

(21) Appl. No.: 14/774,508

(22) PCT Filed: Mar. 14, 2014

(86) PCT No.: PCT/IB2014/059803
§ 371 (c)(1),
(2) Date: Sep. 10, 2015

(87) PCT Pub. No.: WO2014/141177
PCT Pub. Date: Sep. 18, 2014

(65) Prior Publication Data
US 2016/0031815 A1  Feb. 4, 2016

(51) Int. Cl.
| A61K 31/445 | (2006.01) |
| C07D 211/04 | (2006.01) |
| C07D 211/70 | (2006.01) |
| C07D 409/06 | (2006.01) |
| C07D 211/98 | (2006.01) |
| A61K 31/4418 | (2006.01) |
| A61K 31/451 | (2006.01) |
| A61K 45/06 | (2006.01) |
| C07D 211/58 | (2006.01) |

(52) U.S. Cl.
CPC ........ *C07D 211/70* (2013.01); *A61K 31/4418* (2013.01); *A61K 31/451* (2013.01); *A61K 45/06* (2013.01); *C07D 211/58* (2013.01); *C07D 211/98* (2013.01); *C07D 409/06* (2013.01)

(58) Field of Classification Search
CPC ............................ A61K 31/445; C07D 211/04
USPC .......................................... 514/315; 546/184
See application file for complete search history.

(56) References Cited

U.S. PATENT DOCUMENTS 3,171,838 A   3/1965 Janssen 5,296,485 A   3/1994 Lubisch et al.
5,618,822 A   4/1997 Guzzi et al.

FOREIGN PATENT DOCUMENTS

EP        0 490 560 A1   6/1992
EP        0 503 411 A1   9/1992
WO      WO 93/11107 A1   6/1993

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Berrade et al., "Novel Benzo[b]thiophene Derivatives as New Potential Antidepressants with Rapid Onset of Action", Journal of Medicinal Chemistry, vol. 54, XP055069736, 2011, pp. 3086-3090.
Brine et al., "Enantiomers of Diastereomeric cis-N-[I-(2-Hydroxy-2-phenylethyl)-3-methyl-4-piperidyl]-N-phenylpropanamides: Synthesis, X-ray Analysis, and Biological Activities", Journal of Medicinal Chemistry, vol. 38, XP055115780, 1995, pp. 1547-1557.
Brine et al., "Synthesis of 4,4-Disubstituted Piperidine Analogs of (+-31 )-cis-N-[I-(2-Hydroxy-2-phenylethyl)-3-methyl-4-piperidy]-N-phenylpropanamide", Journal of Heterocyclic Chemistry, vol. 31, XP008118826, Mar.-Apr. 1994, pp. 513-520.
Csuzdi et al., "Benzyl Cation Initiated Intramolecular Cyclizations. Synthesis of 1-Azabicyclo[3.2.1]octene Derivatives", Journal für praktische Chemie Chemiker-Zeitung, vol. 340, XP055115778, 1998, pp. 472-475.
Database Registry [Online] Chemical Abstracts Service, Columbus, Ohio, US; Dec. 19, 2007, XP002726637, Database accession No. 958717-95-8; Compounds with Registry No. 958717-95-8; 958708-41-3; 958701-94-5.
Database Registry [Online] Chemical Abstracts Service, Columbus, Ohio, US; Nov. 19, 2004, XP002726638, Database accession No. 784117-96-0; Compound with Registry No. 784117-96-0.
Database Registry [Online] Chemical Abstracts Service, Columbus, Ohio, US; Oct. 22, 2004, XP002726639, Database accession No. 767245-63-6; Compound with Registry No. 767245-63-6.

(Continued)

*Primary Examiner* — Douglas M Willis
(74) *Attorney, Agent, or Firm* — Birch, Stewart, Kolasch & Birch, LLP

(57) ABSTRACT

The present invention relates to new arylaminoalcohol derivatives of formula (I), and to a method for the preparation of such compounds: I The invention also relates to the use of these compounds as medicaments, and in particular for the prevention and/or the treatment of parasitic diseases caused by apicomplexan parasites such as malaria and toxoplasmosis. Finally, the invention relates to pharmaceutical compositions containing such compounds of formula (I) as active principles.

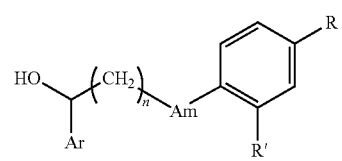

20 Claims, 2 Drawing Sheets

(56) References Cited

OTHER PUBLICATIONS

Database Registry [Online] Chemical Abstracts Service, Columbus, Ohio, US; Mar. 25, 2010, "1(2H)-pyridineethanol, .alpha.-(2,3-dihydro-5-benzofuranyl)-4-(4-fluorophenyl)-3,6-dihydro-", XP002726636, Database accession No. 1214615-13-0; Compounds with Registry No. 1214615-13-0; 1214510-82-3; 1214487-38-3; 1214466-89-3; 1214403-20-9.

Database Registry [Online] Chemical Abstracts Service, Columbus, Ohio, US; Jul. 30, 1996, XP002726640, Database accession No. 178896-99-6; Compound with Registry No. 178896-99-6.

Gizur et al., "Novel 1,2,3,6-tetrahydropyridine derivatives with potent antihypoxic activity", European Journal of Medicinal Chemistry, Elsevier, Paris, FR, vol. 29, XP023870425, 1994, pp. 349-355.

Mendoza et al., "Aryl piperazine and pyrrolidine as antimalarial agents. Synthesis and investigation of structure-activity relationships", Experimental Parasitology, Elsevier, vol. 128, XP028189447, 2011, pp. 97-103.

Púrez-Silanes et al., "New 1-Aryl-3-Substituted Propanol Derivatives as Antimalarial Agents", Molecules, vol. 14, XP055069705, Oct. 14, 2009, pp. 4120-4135.

Sarges et al., "Neuroleptic Activity of Chiral trans-Hexahydro-gamma-carbolines", Journal of Medicinal Chemistry, American Chemical Society, vol. 29, No. 1, XP001037412, 1986, pp. 8-19.

Wang et al., "Stereoisomers of N-[1-(2-Hydroxy-2-phenylethyl)-3-methyl-4-piperidyl]N-phenylpropanamide: Synthesis, Stereochemistry, Analgesic Activity, and Opioid Receptor Binding Characteristics", Journal of Medicinal Chemistry, vol. 38, XP055115783, 1995, pp. 3652-3659.

* cited by examiner

SUBSTITUTED PIPERIDINES WITH ANTIPARASITIC ACTIVITY

CROSS-REFERENCE TO RELATED APPLICATIONS

This application is the National Phase of PCT/IB2014/059803 filed on Mar. 14, 2014, which claims priority under 35 U.S.C. 119 to PCT/IB2013/000982 filed in International Bureau of WIPO on Mar. 15, 2013, all of which are hereby expressly incorporated by reference into the present application.

BACKGROUND OF THE INVENTION

The present invention relates to new arylaminoalcohol derivatives of formula (I) and to a method for the preparation of such compounds. The invention also relates to the use of these compounds as medicaments, and in particular for the prevention and/or the treatment of parasitic diseases caused by apicomplexan parasites such as malaria and toxoplasmosis. Finally, the invention relates to pharmaceutical compositions containing such compounds of formula (I) as active principles.

According to the World Health Organization (World malaria report 2011, http://www.who.int/malaria/world_malaria report_2011/es/index.html), malaria is endemic in 106 countries, affecting more than 200 million people and killing approximately 600.000 people every year, 90% of which are children. Malaria control programs relying on disease prevention and artemisinin-based combination therapies (ACT) have been extremely effective in reducing the disease burden, resulting in a 25% decline in malaria death rates in the last decade, with the highest impact in European countries (99%) while traditionally highly endemic countries of African and American regions report decrease of 33 and 42% respectively. Unfortunately, the emergence of resistance to current treatments and today's global economic situation require a search for new, effective and inexpensive molecules.

Arylaminoalcohols are an important group of compounds with known antimalarial activity and they have been used as antimalarial agents since the 70's. Hydroxylpropyl-piperazine derivatives, belonging to this chemical family, have shown outstanding activity against of *Plasmodium falciparum* chloroquine-resistant strains (A. Mendoza et al., Exp. Parasit. 128(2) (2011) 97-103). According to recent publications (W. Cunico et al., Eur. J. Med. Chem 44 (2009) 1363-1368; W. Cunico et al., Eur. J. Med. Chem 44 (2009) 3816-3820), piperazine derivatives could target *Plasmodium* plasmepsin II enzyme. This enzyme, that recently caused much interest, is involved in the initial steps of the hemoglobin degradation (R. Bruckner, Advanced organic chemistry: reaction mechanisms, Harcout/Academic Press: San Diego, (2002), pp. 636), which is a critical issue in the intra-erythrocytic cycle of the parasite, taking place inside the food vacuole.

Given the small number of available medicaments and the resistance they have already induced, discovery of new targets and of new medicaments remains a key priority. In an effort to discover such new compounds, the Inventors have surprisingly discovered a new class of arylaminoalcohol derivatives of formula (I) showing greater antiplasmodial activity than known arylaminoalcohols. Some of the arylaminoalcohols of the invention inhibit up to 50% of the growth of *Plasmodium falciparum* chloroquine-resistant FCR-3 strain in culture at dose <0.5 Moreover, the arylaminoalcohol derivatives of the invention are active in vivo in murine model.

DETAILED DESCRIPTION OF THE INVENTION

The invention describes a compound of formula (I) below:

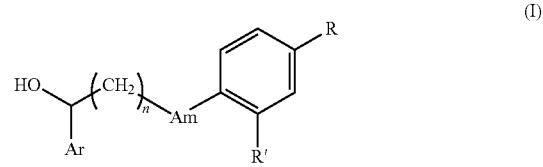

wherein:
Ar is an optionally substituted aromatic group selected from the phenyl, naphtyl and benzo[b]thiophenyl groups,
n is an integer from 0 to 6, and preferably n=2,
Am is an optionally substituted amino entity selected from:

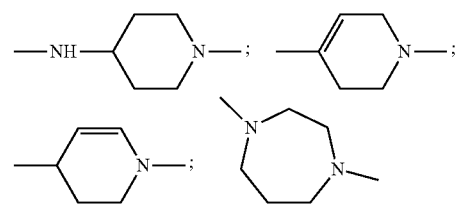

and preferably Am is a tetrahydropyridine entity,
R and R', identical or different, are selected from hydrogen or halogen atoms, —NO$_2$, —CF$_3$.

A first subject of the invention is a compound of formula (I) below:

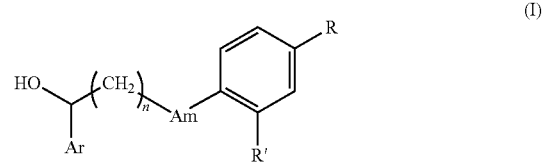

wherein:
Ar is an optionally substituted aromatic group selected from phenyl and naphtyl groups,
n is an integer from 0 to 6, and preferably n=2,
Am is an optionally substituted amino entity selected from:

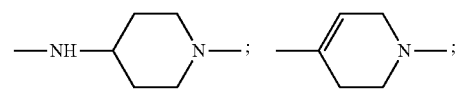

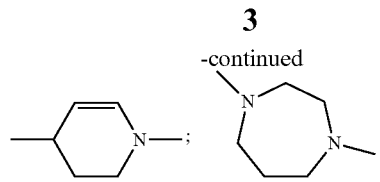

and preferably Am is a tetrahydropyridine entity,
R and R', identical or different, are selected from hydrogen or halogen atoms, —NO$_2$, —CF$_3$.

In the sense of the present invention an aromatic group is either an aryl or a heteroaryl group defined as follows:

Aryl group means any functional group or substituent derived from at least one simple aromatic ring; an aromatic ring corresponding to any planar cyclic compound having a delocalized π system in which each atom of the ring comprises a p-orbital, said p-orbitals overlapping themselves. More specifically, the term aryl includes, but is not limited to, phenyl, biphenyl, 1-naphthyl, 2-naphthyl, anthracyl, pyrenyl, and the substituted forms thereof;

Heteroaryl group means any functional group or substituent derived from at least one aromatic ring as defined above and containing at least one heteroatom selected from P, S, O and N. The term heteroaryl includes, but is not limited to, furan, pyridine, pyrrole, thiophene, imidazole, pyrazole, oxazole, isoxazole, thiazole, isothiazole, tetrazole, pyridazole, pyridine, pyrazine, pyrimidine, pyridazine, benzofurane, isobenzofurane, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine. The aryl and heteroaryl groups of the invention comprise preferably 1 to 12 carbon atoms, and more preferably 5 or 6 carbon atoms.

According to the invention, halogen atoms are chosen among bromine, chlorine, fluorine and iodine, preferably bromine, chlorine and fluorine atoms, and more preferably fluorine atom.

When the groups or entities of the invention are optionally substituted, the substituents may be selected for example from halogen, hydroxyl, cyano, nitro, carboxylate, carboxyester, amino, ketone, $C_1$-$C_{12}$ alkyl, heteroalkyl or alkoxy groups, $C_3$-$C_7$ cycloalkyl group, $C_1$-$C_{12}$ aryl or heteroalkyl groups.

According to a preferred embodiment, the aromatic group Ar is substituted by a halogen atom, preferably a fluorine atom.

The aromatic group Ar is preferably selected from the 4-fluoro-1-phenyl and 4-fluoro-1-naphtyl groups, and more preferably Ar is a 4-fluoro-1-phenyl group.

According to an advantageous embodiment of the invention: R is —NO$_2$ or —F.

According to another advantageous embodiment of the invention: R' is —H or —CF$_3$.

According to a more particularly preferred embodiment: R=—NO$_2$ and R'=CF$_3$.

Another subject matter of the invention is a method for the preparation of a compound of formula (I) according to the invention, comprising the following steps:

(i) a condensation step of a methyl-ketone of formula (IV) with an aryl amine of formula (V) via a Mannich reaction, preferably in presence of dioxolan/H$^+$ and during 1 to 3 hours under reflux:

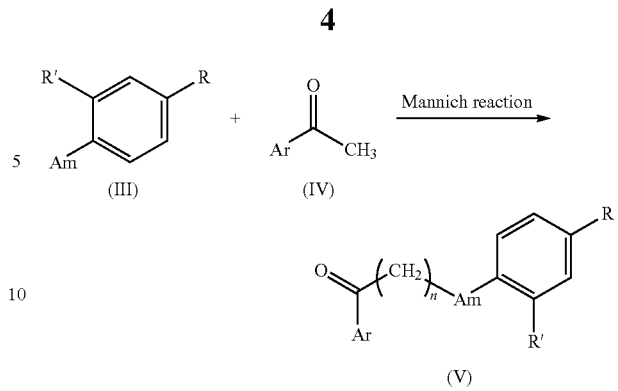

(ii) a reduction step of the ketone intermediate (V) of step (i) to obtain a compound of formula (I), preferably with NaBH$_4$ in methanol and during 0.5 to 2 hours at 0° C.:

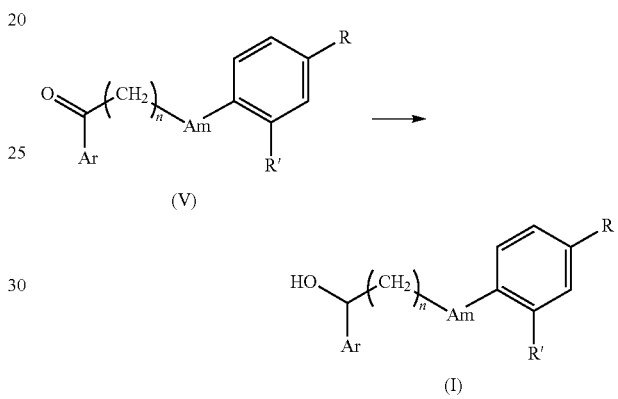

Another subject matter of the invention is a compound of formula (I), or one of its tautomeric, racemic, enantiomeric or polymorphic forms or pharmaceutically acceptable salts, for its use as a medicament, preferably for the prevention and/or the treatment in human and other mammals of parasitic diseases involving apicomplexan parasites, such as *Plasmodium, Babesia, Toxoplasma, Neospora, Cryptosporidium, Theileria, Sarcosystis* and *Eimeria*, and more preferably for the prevention and/or the treatment in human and other mammals of malaria or toxoplasmosis.

The active site of parasitic plasmepsin is similar to HIV protease. This viral protein allows the cleavage of essential proteins for virus replication. A protease inhibitor leads to the inactivation of the protein and stop viral replication. However, and because of the development of a resistance faced to protease inhibitors, an HIV infection can persist despite the presence of a protease inhibitor in the body. Compounds of formula (I) of the invention appear to be useful for the prevention and/or the treatment of AIDS virus.

Another subject matter of the invention is a pharmaceutical composition comprising at least one compound of formula (I) as an active principle, and at least one pharmaceutically acceptable excipient.

The expression "pharmaceutically acceptable excipient" refers to any diluents, adjuvants or vehicles, such as preserving agents, fillers, disintegrating agents, wetting agents, emulsifying agents, suspending agents, solvents, dispersion media, coatings, antibacterial and antifungal agents, isotonic and absorption delaying agents and the like.

The pharmaceutical composition of the present invention may be administered by any suitable route, for example, by oral, buccal, inhalation, sublingual, nasal, percutaneous, i.e. transdermal or parenteral (including intravenous, intramuscular, subcutaneous and intracoronary) administration. Therefore, the pharmaceutical composition of the invention can be provided in various forms, such as in the form of hard gelatin capsules, of capsules, of compressed tablets, of suspensions to be taken orally, of lozenges or of injectable solutions or in any other form appropriate to the method of administration.

The pharmaceutical composition according to the invention includes those wherein a compound of formula (I) is administered in an effective amount to achieve its intended purpose. Determination of the effective amounts is well within the capability of those skilled in the art.

A "therapeutically effective dose" refers to that amount of compound of formula (I) which results in achieving the desired effect. Toxicity and therapeutic efficacy of compound of formula (I) can be easily determined by standard pharmaceutical procedures in cell cultures or experimental animals, i.e. for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. The data obtained from such data can be used in formulating range of dosage for use in humans. The dosage of compound of formula (I) preferably lies within a range of circulating concentrations that include the $ED_{50}$ with little or no toxicity. The dosage can vary within this range depending upon the dosage form employed, and the route of administration.

The exact formulation, route of administration, and dosage can be chosen by the individual physician in view of the patient's conditions. Dosage amount and interval of administration can be adjusted individually to provide plasma levels of compound of formula (I) which are sufficient to maintain the preventive or therapeutic effects.

The amount of pharmaceutical composition administered will therefore depend on the subject being treated, on the subject's weight, the severity of the affliction and the way of administration.

For human and other mammal use, the compounds of formula (I) can be administered alone, but they are preferably administered in admixture with at least one pharmaceutically acceptable carrier, the nature of which will depend on the intended route of administration and the presentation form. Pharmaceutical composition for use according to the present invention thus can be formulated in a conventional manner using one or more physiologically acceptable carriers comprising one or more excipient(s) and/or auxiliary(ies) that facilitate processing of the compounds of formula (I) into preparations which can be used pharmaceutically. Amongst the excipients and auxiliaries which can be used in the pharmaceutical composition according to the invention, one can mention anti-agglomerating agents, preservatives agents, dyes, vitamins, inorganic salts, taste-modifying agents, smoothing agents, coating agents, isolating agents, stabilizing agents, wetting agents, anti-caking agents, dispersing agents, emulsifying agents, aromas, penetrating agents, solubilizing agents, etc., mixtures thereof and generally any excipient conventionally used in the pharmaceutical industry.

By way of example, when the pharmaceutical composition is administered orally, the carrier may comprise one or several excipients such as talc, lactose, starch or modified starches, cellulose or cellulose derivatives, polyethylene glycols, acrylic acid polymers, gelatin, magnesium stearate, animal or vegetal fats of natural or synthetic origin, paraffin derivatives, glycols, etc.

In addition to the at least one compound of formula (I), the pharmaceutical composition may also comprises one or more additional antiparasitic active principles, for example anti-malarial drugs such as for example chloroquine, quinacrine, primaquine, artemisinin, atovaquone and pyrimethamine.

For general information about the formulation and administration of pharmaceutical compositions, one can obviously refer to the book "Remington's Pharmaceutical Sciences", last edition. Of course, a person skilled in the art will take care on this occasion that the excipient(s) and/or auxiliary(ies) optionally used are compatible with the intrinsic properties attached to the pharmaceutical composition in accordance with the invention.

These pharmaceutical compositions can be manufactured in a conventional manner, i.e. by conventional mixing, dissolving, granulating, dragee-making, emulsifying, encapsulating, entrapping or lyophilizing processes. Proper formulation is dependent upon the route of administration chosen.

In addition to the above provisions, the invention also comprises other provisions which will become clear from the description which follows, which refers to examples illustrating the in vitro and in vivo antimalarial activity of compounds of formula (I), and also to the attached drawings in which:

EXAMPLES

Figure 1:
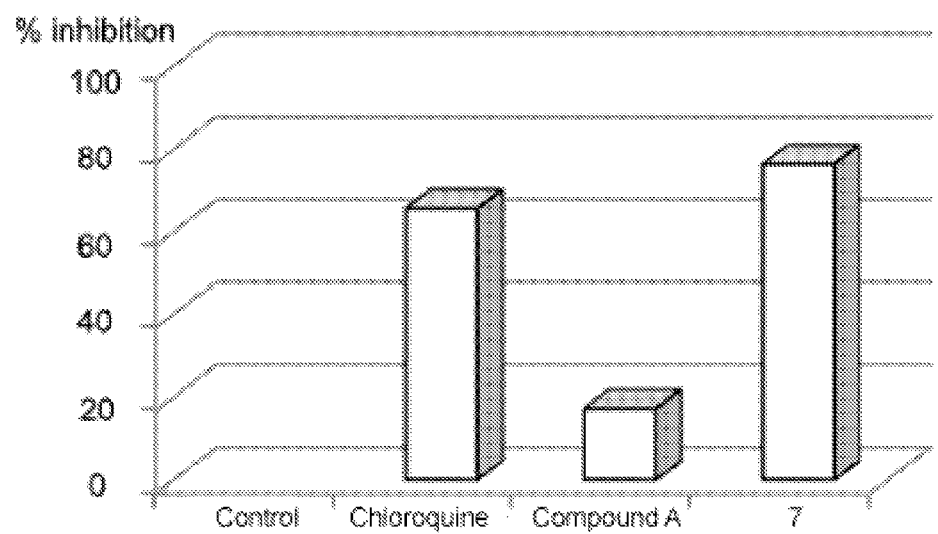
FIG. 1 shows the antimalarial activity of Compound 7 tested in vivo in a murine model.

I/ Chemistry of the Synthesis of Compounds of Formula (I)

The methods used for synthesizing the compounds (1-8) are presented in Schemes 1 and 2. The synthetic method has been published previously (A. Mendoza et al., Exp. Parasit. 128(2) (2011) 97-103).

Scheme 1: Synthesis of not commercially available arylamines

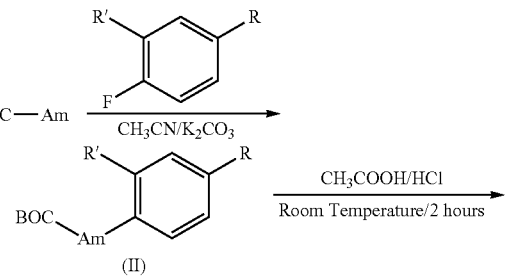

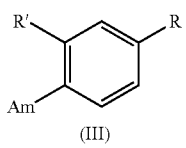

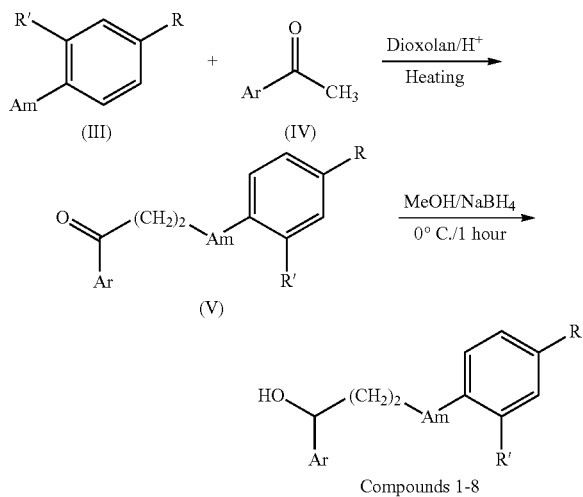

Scheme 2: General synthesis

Compounds 1-8

A group of 4-nitro-2-trifluromethyl phenyl amines were synthesized using the corresponding BOC-amines and 4-nitro-2-trifluoromethylphenyl as aryl fluoride by an Ar—$S_N$ reaction via Meisenheimer complex (K. Ersmark et al., Med. Res. Rev. 26 (2006) 626-666) and subsequent removal of the BOC-group with HCl and acetic acid. The products 2-nitro-4-trifluromethyl phenyl piperazine, 4-(4-fluorophenyl)-1,2,3,6-tetrahydropyridine and 4-trifluoromethyl phenyl piperazine were commercially available.

All methyl-ketone precursors (IV) were commercially available. The ketone intermediates (V) were prepared by condensation of the corresponding methyl-ketone (IV) with the different aryl amines via Mannich reaction.

The hydroxyl derivatives (1-8) were obtained by reduction of the corresponding carbonyl group with NaBH$_4$ in methanol.

II/ Experimental Protocol for the Synthesis of Compounds of Formula (I)

II/1—General Methods

Chemicals reagents were purchased from E. Merck (Darmstadt, Germany), Scharlau (F.E.R.O.S.A., Barcelona, Spain), Panreac Quimica S.A. (Montcada i Reixac. Barcelona, Spain), Sigma-Aldrich Química S.A. (Alcobendas, Madrid), Acros Organics (Janssen Pharmaceuticals 3a, 2440 Geel, Belgie) and Lancaster (Bischheim-Strasbourg, France).

All of the synthesized compounds were chemically characterized by thin layer chromatography (TLC), melting point (M.P.), infrared (IR) and nuclear magnetic resonance ($^1$H-NMR) spectra as well as by elemental microanalysis.

$^1$H NMR spectra were recorded on a Bruker 400 Ultrashield (400 MHz) (Rheinstetten, Germany) using TMS as the internal standard and chloroform (CDCl$_3$) or dimethyl sulfoxide-d$_6$ (DMSO-d$_6$) as solvents. The chemical shifts are reported in ppm (δ) and coupling constant (J) values are given in Hertz (Hz). Signal multiplicities are represented by: s (singlet), bs (broad singlet), d (doublet), t (triplet), q (quadruplet), dd (doublet of doublets), ddd (doublet of doublet of doublets) and m (multiplet). The IR spectra were performed on Thermo Nicolet FT-IR Nexus Euro (Madison, USA) using KBr pellets; the frequencies are expressed in cm$^{-1}$. Elemental microanalyses were obtained on an Elemental Analyzer (LECO CHN-900, Michigan, USA) from vacuum-dried samples. The analytical results for C. H. and N were within ±0.4 of the theoretical values. Alugram SIL G/UV254 (Layer: 0.2 mm) (Macherey-Nagel. Germany) was used for thin layer chromatography and silica gel 60 (0.040-0.063 mm and 0.063-0.200 nm) was used for column flash chromatography (Merck).

Some ketones and hydroxyls were purified by flash chromatography with binary gradient of dichloromethane (synthesis grade SDS-Carlo Erba Reactifs, France) with methanol (Panreac Quimica S.A.) until 99:1 and a UV variable dual—wavelength detection. The chromatography was developed in the CombiFlash® Rf (Teledyne Isco, Lincoln. USA), with dichloromethane—methanol as solvents and a normal phase of 12 gram Flash Column (RediSep® Rf Columns by Teledyne Isco, Inc., USA).

II/2—General Method for the Synthesis of Protected Aryl Amines (II)

A mixture of the 2-fluoro-4-nitrobenzo-trifluoride (1 eq), the corresponding BOC-amine (1.2 eq), K$_2$CO$_3$ (1.5 eq) and CH$_3$CN (30 mL) was heated at reflux for 24 hours. The solvent was removed under reduced pressure. The residue was dissolved in CH$_2$Cl$_2$ (50 mL) and washed with water (3×30 mL). The organic phase was dried with anhydrous Na$_2$SO$_4$ and filtered. After evaporating to dryness under reduced pressure, the residue was precipitated and washed by adding diethyl ether or petroleum ether, affording the desired protected aryl amine (II).

II/3—General Synthesis of Noncommercial Aryl Amines (III)

The protected amine (II) was dissolved in 40 mL of a solution of HCl/AcH (1:1) with stirring for 2 hours at room temperature. The solvent was removed under reduced pressure and the compound was dissolved in water. The aqueous solution was basified with NaOH 2M and stirred for 1 hour. Then the product was extracted with CH$_2$Cl$_2$. The organic phase was dried with anhydrous Na$_2$SO$_4$ and filtered. After evaporating to dryness under reduced pressure, the crude was purified by column chromatography (SP: silica gel), eluting with dichloromethane (NH$_3$)/methanol 99:1 (v/v), affording the desired aryl amine (III).

II/4—General Method for the Synthesis of Ketone Derivatives (V)

A mixture of the appropriately substituted aryl methyl ketone (IV) (1 eq), the aryl amine (III) (1 eq), dioxolane (1.4%) and concentrated HCl (1 mL) was heated at reflux. Then water was added (50 mL) and the product was extracted with CH$_2$Cl$_2$. The organic phase was dried with anhydrous Na$_2$SO$_4$, filtered and evaporating to dryness under reduced pressure. The residue was purified by column chromatography (SP: silica gel), eluting with CH$_2$Cl$_2$/methanol 95:5 (v/v) or Flash Chromatography eluting with CH$_2$Cl$_2$/methanol 99:1 (v/v). In other cases the hydrochloride salt was prepared by adding a hydrogen chloride ethereal solution to the stirred compounds.

II/5—General Method for Preparing of Hydroxyl Derivatives (1-8)

Sodium borohydride (3 eq) was added little by little to a pre-cooled suspension (0° C.) of the corresponding ketone (V) (1 eq) in methanol over a period of 30-60 minutes. The solvent was removed under reduced pressure and the residue was dissolved in dichloromethane (40 mL) and then washed with water (3×30 mL). The organic phase was dried with anhydrous $Na_2SO_4$ and filtered. After evaporating the solvent to dryness under reduced pressure, the compound was purified by column chromatography (SP: silica gel), eluting with dichloromethane/methanol 99:1 (v/v), by preparative chromatography (SP: silica gel), eluting with dichloromethane/methanol 97:3 (v/v), flash chromatography eluting with dichloromethane/methanol 99:1 (v/v) or preparing the hydrochloride by adding a hydrogen chloride ethereal solution to the stirred compounds.

II/5-1. 3-[4-(4-fluorophenyl)-3,6-dihydropyridin-1 (2H)-yl]-1-(naphthalen-2-yl)propan-1-ol (3)

(23% Yield), Mp 127-129° C. $^1$H NMR (400 MHz, $CDCL_3$): δ 1.99-2.12 (m, 2H, CHOH—$CH_2$); 2.64 (s, 2H, $H_6$ tetrahydropyridine); 2.72-2.96 (m, 4H, $H_3$+$H_5$ tetrahydropyridine); 3.31 (d, 2H, CHOH—$CH_2$—$CH_2$, $J_{CH-CH2}$=16.7 Hz); 5.17 (bs, 1H, CH—OH); 6.02 (s, 1H, $H_3$ tetrahydropyridine); 7.04 (t, 2H, $H_3$'+$H_5$' phenyl, $J_{3',2'}$=$J_{5',6'}$=8.7 Hz); 7.37 (dd, 2H, $H_2$'+$H_6$' phenyl, $J_{2',3'}$=$J_{6',5'}$=8.7 Hz, $J_{2',F}$=$J_{6',F}$=5.4 Hz); 7.45-7.50 (m, 2H, $H_6$+$H_7$ naphtyl); 7.51 (dd, 1H, $H_8$ naphtyl, $J_{8,7}$=7.4 Hz, $J_{8,6'}$=1.6 Hz); 7.85 (d, 2H, $H_3$+$H_4$ naphtyl, $J_{3,4}$=$J_{4,3}$=8.3 Hz); 7.87 (dd, 1H, $H_5$ naphtyl, $J_{5,6}$=7.8 Hz, $J_{5,7}$=2.3 Hz); 7.91 (s, 1H, $H_1$ naphtyl) ppm. Anal ($C_{24}H_{24}NFO$) C, 77.83; H, 6.62; N, 3.78. Found: C, 77.87; H, 6.82; N, 3.40.

II/5-2. 3-[4-(4-fluorophenyl)-3,6-dihydropyridin-1 (2H)-yl]-1-(4-(trifluoromethyl phenyl)propan-1-ol) (4)

(40% Yield), Mp 116-117° C. $^1$H NMR (400 MHz, DMSO): δ 1.81 (dd, 2H, CHOH—$CH_2$, $J_{CH-CH2}$=13.7 Hz, $J_{CH-CHOH}$=7.3 HZ); 2.45-2.50 (m, 4H, CHOH—$CH_2$—$CH_2$+$H_5$ tetrahydropyridine); 2.62 (t, 2H, $H_6$ tetrahydropyridine, $J_{CH-CH}$=$J_{CH-CH2}$=5.5 Hz); 3.08 (s, 2H, $H_2$ tetrahydropyridine); 4.75-4.80 (m, 1H, CHOH); 5.70 (bs, 1H, OH); 6.12 (s, 1H, $H_3$ tetrahydropyridine); 7.15 (t, 2H, $H_5$'+$H_3$' phenyl, $J_{5',F}$=$J_{3',F}$=8.8 Hz, $J_{5,6'}$=$J_{3',2'}$=8.8 Hz); 7.47 (dd, 2H, $H_6$'+$H_2$' phenyl, $J_{6',5'}$=$J_{2',3'}$=8.4 Hz, $J_{6',F}$=$J_{2',F}$=5.6 Hz); 7.57 (d, 2H, $H_2$+$H_6$ $CF_3$-phenyl, $J_{2,3}$=$J_{6,5}$=7.9 Hz); 7.68 (d, 2H, $H_3$+$H_5$ $CF_3$-phenyl, $J_{3,2}$=$J_{5,6}$=8.1 Hz) ppm. Anal ($C_{21}H_{21}NF_4O$) C, 66.49; H, 5.54; N, 3.70. Found: C, 66.11; H, 5.67; N, 3.81.

II/5-3. 1-(4-fluoronaphthalen-1-yl)-3-((1-(4-nitro-2-(trifluoromethyl) phenyl) piperidin-4-yl)amino)propan-1-ol (5)

(90% Yield), Mp 93-95° C. $^1$H NMR (400 MHz. $CDCl_3$): δ 1.68-1.83 (m, 2H, $H_{3ax}$+$H_{5ax}$ piperidine); 1.86-2.01 (m, 1H, CHOH—$CH_2$); 2.15-2.23 (m, 2H, $H_{3ec}$+$H_{5ee}$ piperidine); 2.12 (d, 2H, CH—OH. $J_{CH-CH2}$=12.7 Hz); 2.75-2.84 (m, 1H, $H_4$ piperidine); 2.98 (t, 2H, $H_{2ax}$+$H_{6ax}$ piperidine, $J_{2ax,2ec}$=$J_{6ax,6ec}$=11.5 Hz); 3.00-3.03 (m, 1H, CHOH—$CH_2$—$CH_2$); 3.08-3.15 (m, 1H, CHOH—$CH_2$—$CH_2$); 3.42 (d, 2H, $H_{2ec}$+$H_{6ec}$ piperidine, $J_{CH,CH2}$=8.2 HZ, $J_{CH-CH2}$=2.3 Hz); 7.17 (dd, 1H, $H_3$ naphtyl, $J_{3,F}$=10.2 Hz, $J_{3,2}$=8.1 Hz); 7.27-7.30 (m, 1H, $H_6$' phenyl); 7.53-7.61 (m, 2H, $H_6$+$H_7$ naphtyl); 7.67-7.72 (m, 1H, $H_2$ naphtyl); 8.04 (d, 1H, $H_8$ naphtyl, $J_{8,7}$=7.8 Hz); 8.16 (dd, 1H, $H_5$ naphtyl $J_{5,6}$=7.2 Hz, $J_{5,7}$=3.3 Hz); 8.33 (dd, 1H, $H_5$' phenyl, $J_{5',6}$=9.0 Hz, $J_{5',3}$=2.7 Hz); 8.53 (d, 1H, $H_3$' phenyl, $J_{3',5'}$=2.7 Hz). ppm. Anal ($C_{25}H_{25}N_3F_4O_3$) C, 61.11; H, 5.43; N, 8.55. Found: C, 60.77; H, 5.43; N, 8.30.

II/5-4. 1-(4-fluoronaphthalen-1-yl)-3-[4-(4-fluorophenyl)-3,6-dihydropyridin-1(2H)-yl]propan-1-ol (6)

(82% Yield), Mp 162-163° C. $^1$H NMR (400 MHz. DMSO): δ 2.14-2.20 (m, 2H, CHOH—$CH_2$); 2.73 (bs, 2H, $H_6$ tetrahydropyridine); 2.84-3.12 (m, 4H, CHOH—$CH_2$—$CH_2$+$H_5$ tetrahydropyridine); 3.41 (d, 1H, $H_{2ax}$ tetrahydropyridine, $J_{2ax,2ec}$=11.2 Hz); 3.47 (d, 1H, $H_{2ec}$ tetrahydropyridine); $J_{2ec,2ax}$=11.3 Hz); 5.74 (bs, 1H, CHOH); 6.00-6.05 (m, 1H, $H_3$ tetrahydropyridine); 7.00-7.08 (m, 2H, $H_2$'+$H_6$' phenyl); 7.18 (dd, 1H, $H_3$ naphtyl, $J_{3,F}$=10.2 Hz, $J_{3,2}$=8.1 Hz); 7.35-7.40 (m, 2H, $H_6$+$H_7$ naphtyl); 7.54-7.61 (m, 2H, $H_5$'+$H_3$' phenyl); 7.70 (dd, 1H, $H_2$ naphtyl, $J_{2,3}$=8.0 Hz, $J_{2,F}$=5.6 Hz); 8.07 (d, 1H, $H_5$ naphtyl, $J_{5,6}$=8.2 Hz); 8.2 (dd, 1H, $H_8$ naphtyl, $J_{8,7}$=7.0 Hz, $J_{8,6}$=2.5 Hz) ppm. Anal ($C_{24}H_{23}NF_2O$) C, 75.95; H, 6.06; N, 3.69. Found: C, 75.45; H, 6.45; N, 3.50.

II/5-5. Hydrochloride of 1-(4-fluorophenyl)-3-[1-(4-nitro-2-trifluoromethylphenyl) piperidin-4-yl)amino] propan-1-ol (7)

(11% Yield), Mp 185-187° C., $^1$H NMR (400 MHz, DMSO): δ 1.38 (bs, 2H, $H_{3ax}$+$H_{5ax}$ piperidine); 1.70 (bs, 2H, $H_{3ec}$+$H_{5ec}$ piperidine); 1.90 (d, 2H, CHOH—$CH_2$, $J_{CH-CH}$=$J_{CH-CH2}$=11.0 Hz); 2.58 (bs, 1H, $H_4$ piperidine); 2.63-2.64 (m, 2H, $H_{2ax}$+$H_{6ax}$ piperidine); 2.95 (t, 2H, $H_{2ec}$+$H_{6ec}$ piperidine, $J_{2ec,2ax}$=$J_{6ec,6ax}$=12.1 Hz); 3.2-3.3 (m, 2H, CHOH—$CH_2$—$CH_2$); 4.69 (t, 1H, CHOH, $J_{CHOH-CHCH}$=9.0 Hz); 7.13 (t, 2H, $H_3$+$H_5$ fluorophenyl, $J_{3,2}$=$J_{5,6}$=8.1 Hz); 7.36 (bs, 2H, $H_2$+$H_6$ fluorophenyl); 7.50 (d, 1H, $H_6$' phenyl, $J_{6',5'}$=8.0 Hz); 8.37 (bs, 2H, $H_3$'+$H_5$' phenyl) ppm. Anal ($C_{21}H_{25}N_3ClF_4O_3$) C, 52.51; H, 5.03; N, 8.80. Found: C, 52.13; H, 4.91; N, 8.49.

II/5-6. 1-(4-fluorophenyl)-3-[4-(4-fluorophenyl)-3,6-dihydropyridin-1 (2H)-yl]propan-1-ol (8)

(12% Yield), Mp 199-201° C. $^1$H NMR (400 MHz, DMSO): δ 1.76-1.80 (m, 2H, CHOH—$CH_2$); 2.45 (bs, 4H, CHOH—$CH_2$—$CH_2$+$H_5$ tetrahydropyridine); 2.57-2.62 (m, 2H, $H_6$ tetrahydropyridine); 3.06 (bs, 2H, $H_2$ tetrahydropyridine); 4.66 (t, 1H, CHOH. $J_{CH-OH}$=6.3 Hz); 5.49 (bs, 1H, OH); 6.12 (bs, 1H, $H_3$ tetrahydropyridine); 7.14 (dd, 4H, $H_3$'+$H_5$' phenyl+$H_3$+$H_5$ fluorophenyl, $J_{3',F}$=$J_{5',F}$=$J_{3,F}$=$J_{5,F}$=12.6 Hz, $J_{3',2}$=$J_{5',6}$=$J_{3,2}$=$J_{5,6}$=8.0 Hz); 7.37 (dd, 2H, $H_2$+$H_6$ fluorophenyl, $J_{2,3}$=$J_{6,5}$=7.9 Hz, $J_{2,F}$=$J_{6,F}$=6.0 Hz); 7.46 (dd, 2H, $H_2$'+$H_6$' phenyl, $J_{2',3'}$=$J_{6',5'}$=7.7 Hz, $J_{2',F}$=$J_{6',F}$=5.5 Hz) ppm. Anal ($C_{20}H_{21}NF_2O$) C, 72.42; H, 6.34; N, 4.22. Found: C, 72.06; H, 6.33; N, 4.03.

III/ Biological tests

III/1—In Vitro Antiplasmodial Drug Assay

Culture of chloroquine-resistant FCR-3 strain of *Plasmodium falciparum* was carried out at 37° C. in a 5% $CO_2$ environment on RPMI 1640 medium supplemented with 25 mM Hepes, 5% (w/v) $NaHCO_3$, gentamicin 0.1 mg/ml and 10% heat-inactivated human serum A$^+$ (hematocrit 5%), as previously described (W. Trager et al., Science, 193 (1976) 673-675). The drugs dissolved in dimethylsulfoxide (DMSO) were added at final concentrations ranging from 200 to 0.1 μM. All experiments were performed in triplicate. The final DMSO concentration was never greater than 0.1%. In vitro antimalarial activity was measured using [$^3$H]- hypoxanthine (MP Biomedicals, USA) incorporation assay (R. E. Desjardins et al., Antimicrob. Agents Chemother. 16 (1979) 710-718). All experiments were performed in triplicate. Results were expressed as the concentration resulting in 50% inhibition ($IC_{50}$) which was calculated by linear interpolation (W. Huber et al., Acta Trop. 55 (1993) 257-261) as follows:

$$\text{Log}(IC_{50}) = \log(X1) + (50-Y1)/(Y2-Y1)[\text{Log}(X2) - \log(X1)]$$

X1: concentration of the drug that gives a % inhibition of the parasitemia Y1>50%, X2: concentration of the drug that gives a % inhibition of the parasitemia Y2<50%, % Inhibition of the incorporation of labeled hypoxanthine=100−(P/T*100), P: c.p.m. for every concentration, and T: negative control (red blood cells without drug).

The results are presented in Table 1:

III/2—In Vivo Antiplasmodial Drug Assay

The antiplasmodial activity of Compound 7 was tested in vivo in a murine model. The antiplasmodial activity of a Compound A representative of the prior art was also tested:

Compound A: HO-CH(4-F-phenyl)-(CH$_2$)$_2$-N(piperazine)-N-(2-CF$_3$-4-NO$_2$-phenyl)

TABLE 1

In vitro antimalarial activity against *Plasmodium falciparum* FCR-3 and VERO cytotoxicity of tested compounds

| Compounds | Ar | Amine | R | R' | $IC_{50}$ | $TC_{50}$ |
|---|---|---|---|---|---|---|
| 3 | 2-naphthyl | 1,2,3,6-tetrahydropyridin-4-yl | F | H | 36.15 | >100 |
| 4 | 4-trifluoromethyl phenyl | 1,2,3,6-tetrahydropyridin-4-yl | F | H | 5.60 | >100 |
| 5 | 4-fluoro-1-naphthyl | 4-aminopiperidin-1-yl (—HN) | NO$_2$ | CF$_3$ | 0.15 | 5.5 |
| 6 | 4-fluoro-1-naphthyl | 1,2,3,6-tetrahydropyridin-4-yl | F | H | 0.40 | >50 |
| 7 | 4-fluoro-1-phenyl | 4-aminopiperidin-1-yl (—HN) | NO$_2$ | CF$_3$ | 0.48 | 30.2 |
| 8 | 4-fluoro-1-phenyl | 1,2,3,6-tetrahydropyridin-4-yl | F | H | 0.66 | >100 |
| CQ | | | | | 0.13 | >50 |

CQ: chloroquine; $IC_{50}$ and $TC_{50}$ values represent of 50% of *Plasmodium falciparum* growth or VERO cells survival. Data represents the average of three independent determinations and are expressed in μM. Errors for individual measurements differed by less than 50%.

Studies were conducted according to the French and Colombian guidelines on laboratory animal use and care (No 2001-464 and No 008430, respectively). The classical 4-day suppressive test was carried out (W. Peters, Chemotherapy and drug resistance in malaria, Academic Press: London, 1970). Swiss male mice weighing 20±2 g, were infected with $10^7$ *P. berghei* ANKA parasitized cells (day 0). Two hours after infection and at the same time during 4 consecutive days, batches of three mice were orally treated at dose of 50 mg/kg/day, (drugs were dissolved in vehicle water dimethylsulfoxide 9:1). A control group received the vehicle while a reference group was administered chloroquine diphosphate (CQ) at 3 mg/kg/day (oral route). Survival of the mice was checked daily and the percentage of parasitized erythrocytes was determined on day 4, by Giemsa-stained thin blood smears made from peripheral blood. The percentage of inhibition of parasitaemia was calculated.

The results are presented on FIG. 1.

Compound 7 shows, at 50 mg/kg/day, 76% of inhibition while chloroquine reference dosed at 3 mg/kg/day shows 65% of inhibition and Compound A shows, at 50 mg/kg/day, 17% of inhibition.

III/3—Toxicity Assay

VERO cells (African Green Monkey kidney epithelial cells) were seeded ($5\times10^5$ cells/ml, 100 µl/well) in a 96-well flat-bottom plate at 37° C. and with 5% $CO_2$ in RPMI 1640 without phenol red (Sigma), supplemented with 10% heat-inactivated fetal bovine serum. Drugs were added at different concentrations and the cells were cultured for 48 hours. The effect was determined using the 3-(4,5-dimethylthiazol-2-yl)-2,5-diphenyltetrazolium bromide (MTT) viability assay. Four hours after the addition of MTT, 100 µl of lysis buffer (50% isopropanol, 30% water, 20% SDS) were added and the cells were incubated at room temperature for 15 min under agitation. Finally, optical density was read at 590 nm with a 96-well scanner (Bio-Rad). All experiments were performed in triplicate. The $TC_{50}$ determined by linear regression analysis was defined as the concentration of test sample resulting in a 50% reduction of absorbance when compared with controls.

The results are presented in Table 1.

III/4—Cytoxicity

The cytotoxicity of Compound 7 was compared to the cytotoxicity of Compound 31 of the publication of Silvia Perez-Silanes et al., Molecules 2009, 14, 4120-4135, the compounds only differentiated by the nature of the Ar group (4-fluoro-1-phenyl group vs benzo[b]thiophenyl).

Both compounds were administered at 50 mg·$kg^{-1}$ in a malaria murine model. No cytotoxicity was detected after administration of Compound 7, while more than half of the treated mice died when exposed to Compound 31 of Silvia Perez-Silanes et al.

The too high cyctotoxicity of Compound 31 of Silvia Perez-Silanes et al. indicates that this compound cannot be administered in human or animal, whereas the lowest cytotoxicity of Compound 7 allows a safe administration in mouse.

IV/ Physicochemical Parameters

Virtual Computational Chemistry Laboratory (http://www.vcclab.org/) (I. V. Tetko et al., J. Comput.-Aided Mol. Des. 19 (2005) 453-463) and Molispiration online property calculation toolkit (http://www.molispiration.com/services/properties.html) were used to calculate Topological Polar Surface Area (P. Ertl et al., J. Med. Chem. 43 (2000) 3714-3717) mi Log P, AlogPS2.1, KOWLog P, Log P (AB/Log P), number of rotable bonds and violations of Lipinski's rule of five (C. A. Lipinski et al., Adv. Drug Deliv. Rev. 23 (1997) 3-25).

Absorption (% ABS) was calculated by: % ABS=109-(0.345×TPSA) (Y. Zhao et al., Pharmaceutical Research, 19 (2002) 1446-1457).

The results are presented in Table 2.

TABLE 2

Physical chemical properties of tested compounds

| Compounds | % ABS | TPSA ($Å^2$) | n-ROTB | Molecular weight | miLogP | KOW LogP | ALog PS 2.1 | MLogP | n-OHNH donors | n-ON acceptors | Lipinski's violations |
|---|---|---|---|---|---|---|---|---|---|---|---|
| Rule | | | | >500 | <5 | <5 | <5 | <4.15 | <5 | <10 | ≤1 |
| 3 | 100.00 | 23.47 | 5 | 361.46 | 4.76 | 5.48 | 4.66 | 4.57 | 1 | 2 | 0 |
| 4 | 100.00 | 23.47 | 6 | 379.74 | 4.47 | 5.26 | 4.69 | 4.68 | 1 | 2 | 0 |
| 5 | 80.95 | 81.32 | 8 | 491.47 | 5.36 | 5.76 | 4.65 | 4.86 | 2 | 6 | 1 |
| 6 | 100.00 | 23.47 | 5 | 379.45 | 4.85 | 5.68 | 4.88 | 4.95 | 1 | 2 | 0 |
| 7 | 80.95 | 81.32 | 8 | 443.44 | 4.24 | 4.59 | 3.74 | 4.19 | 2 | 6 | 0 |
| 8 | 100.00 | 23.47 | 5 | 329.39 | 3.74 | 4.50 | 3.95 | 4.25 | 1 | 2 | 0 |
| CQ | 99.30 | 28.20 | 8 | 319.90 | 5.01 | 4.50 | 5.28 | 3.52 | 1 | 3 | 1 |

% ABS: percentage of absorption, calculated by: % ABS = 109 − (0.345 × TPSA);
TPSA: topological polar surface area;
n-ROTB: number of rotatable bonds;
LogP: logarithm of compound partition coefficient between n-octanol and water;
n-OHNH: number of hydrogen bond donors;
n-ON: number of hydrogen bond acceptors.
CQ: chloroquine It appears that all the compounds respected Lipinski's rules (Log P<5, under 5 H-bond donors and 10H-bond acceptors) (C. A. Lipinski at al., Adv. Drug Deliv. Rev. 23 (1997) 3-25). All the structures have a molecular weight under 500 Daltons with limited lipophilicity. Calculated absorption (% ABS) suggests good aptitudes for oral treatment.

V/ Computational Docking Studies

In previous studies using computational molecular binding tools, the enzyme *Plasmodium* plasmepsin II was proposed as a potential target for arylaminoalcohols (A. Mendoza et al., Exp. Parasit. 128(2) (2011) 97-103). This study suggested that the activity of arylaminoalcohol derivatives could be due to the formation of a hydrogen bond with one of the catalytic aspartates from the active site (Asp214 and Asp34). This interaction involves the unique hydroxyl group present in the most active compounds and Asp 214 residue.

The molecular docking program ICM (ICM. Version 3.4-8. La Jolla. Calif. Molsoft LLC. 2006) was used to determine the potential binding mode between the most active synthesized compounds and the selected *Plasmodium* plasmepsin II enzyme target candidate. In order to validate our methodology and check the ability of the program ICM to investigate the binding mode of inhibitors into the binding site of the enzyme, the complex *Plasmodium* plasmepsin II with EH58 (O. A. Asojo et al., J. Mol. Biol. 327 (2003) 173-181) was computationally re-docked (PDB code 1LF3). As previously reported (W. Cunico et al., Eur. J. Med. Chem. 44 (2009) 1363-1368; W. Cunico et al., Eur. J. Med. Chem. 44 (2009) 3816-3820), RMSD values up to 3.0 Å were considered correctly docked structures for preparing the input structures for ICM methodology (R. Abagyan et al., J. Comput. Chem., 15(5) (1994) 488-506). The structures of the compounds were sketched by using the ICM software, Molecular Editor (Molecular Editor. Version 2.5. La Jolla. Calif. Molsoft LLC. 2006). Protein and compound structures were converted into ICM objects. During the protein conversion process, hydrogens were added and the modified structure was optimized. Meanwhile, during ligand conversions, two-dimensional (2D) representations were converted into three-dimensional (3D) ones, partial charges were assigned, and rotatable bonds were identified. According to previous studies (A. Mendoza et al., Exp. Parasit. 128(2) (2011) 97-103; W. Cunico et al., Eur. J. Med. Chem. 44 (2009) 1363-1368; W. Cunico et al., Eur. J. Med. Chem. 44 (2009) 3816-3820), the residues involved in the active site were Asp34 and Asp214. IcmPocketFinder (J. An et al., Mol. Cell. Prot. 4(6) (2005) 752-761) was used to identify the active site pocket with a tolerance value of 4.6 Å. Initial ligand position and orientation and box position and size were maintained in accordance with the values suggested by the program. The most representative binding modes calculated with at least one hydrogen bond with one of the catalytic aspartates were chosen for analysis (V. Kasam et al., J. Chem. Inf. Model. 47(5) (2007) 1818-1828; J. Aqvist et al., Prot. Eng. 7 (1994) 385-391). The docking poses for each ligand were analyzed by examining their relative total energy score. The more energetically favorable conformation was selected as the best pose.

Figure 2:
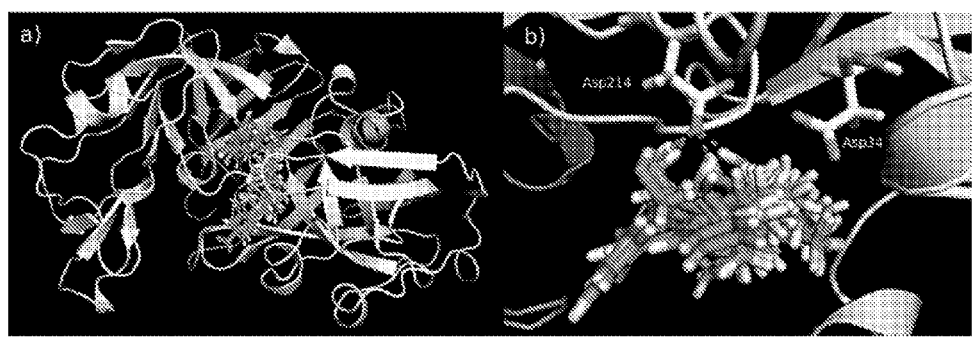
FIG. 2 represents the dockings and binding site alignments of arylaminoalcohols to plasmepsin II. (a) Docking of the most active compound previously reported (A. Mendoza et al., Exp. Parasit. 128(2) (2011) 97-103), and the best conformations found for Compounds 5, 7 and 8 to the active site of plasmepsin II. In white ribbon, the secondary structure of plasmepsin II is shown. (b) Involving the hydroxyl group of each arylaminoalcohol and the residue Asp214, hydrogen bond interactions are coded by dashed lines. In white sticks, catalytic residues Asp214 and Asp34 of plasmepsin II are shown.

The comparison of the different docking results between Compounds 5, 7 and 8 and the most active compound previously reported, i.e. the 1-(4-fluoronaphthalen-1-yl)-3-[4-(4-nitro-2-trifluoromethylphenyl)piperazin-1-yl]propan-1-ol (Compound 13 of A. Mendoza et al., Exp. Parasit. 128(2) (2011) 97-103), revealed that presumably all compounds adopt the same binding mode (FIG. 2a) and establish a hydrogen bond between the hydroxyl group and Asp214 (FIG. 2b).

This similar binding mode is not surprising since all of the tested compounds contain related scaffolds. In general, all these compounds are situated near the S1', S1 and S3 pockets of the protein. 4-nitro-2-trifluoromethyl phenyl and 4-trifluoromethyl phenyl groups of these conformations were set near S1 and S3 pocket, and 4-fluoro-1-phenyl and 4-fluoro-1-naphtyl were located in the vicinity of the S2 pocket.

The invention claimed is:
1. A compound of formula (I):

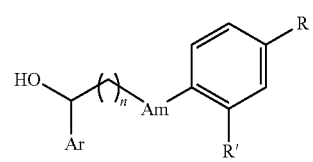

wherein:
n is 2;
Ar is phenyl or naphthyl, each optionally substituted by $CF_3$, F, Cl, Br or I;
Am is selected from:

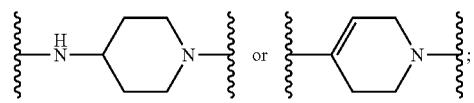

R is selected from H, F, Cl, Br, I, $NO_2$ or $CF_3$; and
R' is selected from H, F, Cl, Br, I, $NO_2$ or $CF_3$.

2. The compound according to claim 1, wherein Ar is substituted by one F.

3. The compound according to claim 2, wherein Ar is 4-fluorophenyl or 4-fluoro-1-naphthyl.

4. The compound according to claim 3, wherein Ar is 4-fluorophenyl.

5. The compound according to claim 1, wherein Am is:

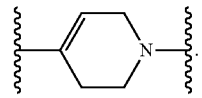

6. The compound according to claim 2, wherein Am is:

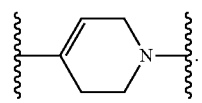

7. The compound according to claim 3, wherein Am is:

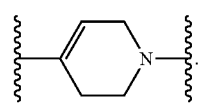

8. The compound according to claim 1, wherein R is $NO_2$ or F.

9. The compound according to claim 2, wherein R is $NO_2$ or F.

10. The compound according to claim 1, wherein R' is H or $CF_3$.

11. The compound according to claim 1, wherein R is $NO_2$ and R' is $CF_3$.

12. A pharmaceutical composition comprising at least one compound according to claim 1 as an active principle and at least one pharmaceutically acceptable excipient.

13. The pharmaceutical composition of claim 12, further comprising at least one additional antiparasitic active principle.

14. The pharmaceutical composition of claim 13, wherein the additional antiparasitic active principle is selected from the group consisting of chloroquine, quinacrine, primaquine, artemisinin, atovaquone and pyrimethamine.

15. A method for treating apicomplexan parasitic activity in a mammal, comprising administering to a mammal in need thereof an effective amount of the compound according to claim 1.

16. The method according to claim 15, wherein the apicomplexan parasite is selected from the group consisting of *Plasmodium, Babesia, Taxoplasma, Neospora, Cryyptosporidium, Theileria, Sarcosystis* and *Eimeria*.

17. The method according to claim 15, wherein the mammal suffers from a parasitic disease involving an apicomplexan parasite.

18. The method according to claim 17, wherein the parasitic disease involving an apicomplexan parasite is malaria.

19. The method according to claim 17, wherein the parasitic disease involving an apicomplexan parasite is toxoplasmosis.

20. A method for the preparation of a compound of formula (I) according to claim 1 where n is 2, comprising the following steps:

(i) reacting a compound of formula (III):

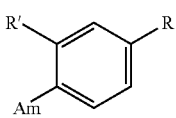

with a compound of formula (IV):

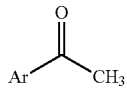

in the presence of dioxolane and acid, to provide a compound of formula (V):

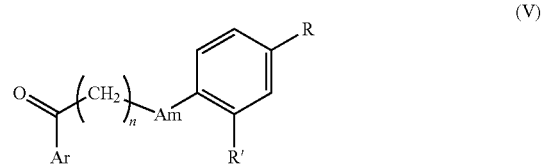

wherein n is 2; and (ii) reacting the compound of formula (V):

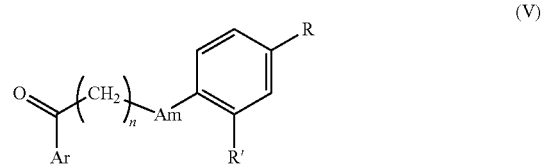

wherein n is 2;

with sodium borohydride, in the presence of methanol, to provide a compound of formula (I):

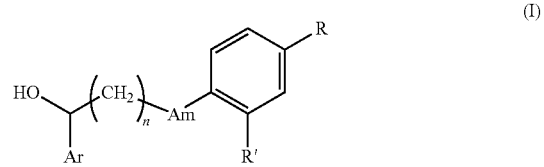

wherein n is 2.

* * * * *